United States Patent
Yan (10) Patent No.: US 10,463,318 B2
(45) Date of Patent: Nov. 5, 2019

(54) MULTI-SEQUENCE SCANNING (71) Applicant: SHENYANG NEUSOFT MEDICAL SYSTEMS CO., LTD., Shenyang (CN)

(72) Inventor: Gang Yan, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 197 days.

(21) Appl. No.: 15/658,287

(22) Filed: Jul. 24, 2017

(65) Prior Publication Data
US 2018/0020994 A1 Jan. 25, 2018

(30) Foreign Application Priority Data

Jul. 25, 2016 (CN) .......................... 2016 1 0589817

(51) Int. Cl.
A61B 6/03 (2006.01)
A61B 6/00 (2006.01)
G06T 11/00 (2006.01)
A61B 6/02 (2006.01)

(52) U.S. Cl.
CPC .............. A61B 6/032 (2013.01); A61B 6/467 (2013.01); A61B 6/5211 (2013.01); A61B 6/5235 (2013.01); A61B 6/5241 (2013.01); G06T 11/005 (2013.01); A61B 6/027 (2013.01); A61B 6/469 (2013.01)

(58) Field of Classification Search
CPC ........ A61B 6/032; A61B 6/467; A61B 6/5211
See application file for complete search history.

(56) References Cited

U.S. PATENT DOCUMENTS

| 2007/0217567 | A1* | 9/2007 | Noshi | A61B 6/032 378/4 |
| 2010/0239146 | A1 | 9/2010 | Suzuki | |
| 2010/0290707 | A1 | 11/2010 | Wang et al. | |
| 2013/0116537 | A1 | 5/2013 | Sato | |
| 2016/0256127 | A1* | 9/2016 | Lee | A61B 6/032 |

FOREIGN PATENT DOCUMENTS

| CN | 102753993 A | 10/2012 |
| CN | 105078495 A | 11/2015 |
| CN | 105389788 A | 3/2016 |
| TW | 201530127 A | 8/2015 |

OTHER PUBLICATIONS

State Intellectual Property Office of the People's Republic of China, Office Action and Search Report Issued in Application No. 201610589817.6, dated Oct. 9, 2018, 12 pages. (Submitted with Partial Translation).

* cited by examiner

Primary Examiner — Hugh Maupin
(74) Attorney, Agent, or Firm — McCoy Russell LLP (57) ABSTRACT A method and device for multi-sequence scanning are provided. According to an example of the method, when at least two mergeable scanning sequences are obtained from a plurality of scanning sequences, a target scanning area including respective scanning areas of the at least two mergeable scanning sequences may be determined; and then a scanning on the target scanning area may be performed with the at least two mergeable scanning sequences. As at least two scanning sequences satisfying a preset mergeable condition may be extracted from a plurality of scanning sequences, the at least two scanning sequences satisfying the preset mergeable condition may be performed at once.

13 Claims, 7 Drawing Sheets

FIG. 1 moving direction of
a scanning bed

MULTI-SEQUENCE SCANNING

CROSS-REFERENCE TO RELATED APPLICATIONS

This application claims priority to Chinese Patent Application No. 201610589817.6 entitled "METHOD AND DEVICE FOR MULTI-SEQUENCE SCANNING," filed on Jul. 25, 2016, the entire contents of which are incorporated herein by reference for all purposes.

BACKGROUND

The present disclosure relates to multi-sequence scanning.

Helical scanning is one of the scanning modes of Computed Tomography (CT). During helical scanning, an X-ray tube and a detector rotate continuously around a long axis of a subject at a constant speed, and a scanning bed is progressive synchronously at a constant speed. Since the scanning trajectory is helical, it is referred to as helical scanning.

For performing a helical scanning on a subject, one or more scanning sequences may be set by a user for a region to be examined of the subject. Then, the CT device will scan the region to be examined according to respective scanning sequences.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and areas around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

An exemplary example will be described in detail herein, examples of which are shown in the accompanying drawings. When the following description refers to the accompanying drawings, the same numerals in the different drawings denote the same or similar elements unless otherwise indicated. The implements described in the following example are not representative of all implements consistent with the present disclosure. In contrast, they are merely examples of devices and methods consistent with some aspects of the present disclosure as detailed in the appended claims.

The terminology used in the present disclosure is for the purpose of describing particular examples only, and is not intended to be limiting of the present disclosure. The singular forms such as "a", "said", and "the" used in the present disclosure and the appended claims are also intended to include multiple, unless the context clearly indicates otherwise. It is also to be understood that the term "and/or" as used herein refers to any or all possible combinations that include one or more associated listed items.

It is to be understood that although different information may be described using the terms such as first, second, and third in the present disclosure, these information should not be limited to these terms. These terms are used only to distinguish the same type of information from each other. For example, the first information may also be referred to as the second information without departing from the scope of the present disclosure, and similarly, the second information may also be referred to as the first information. Depending on the context, in addition, the used word "if" may be interpreted as "when" or "as" or "determining in response to".

A user may set a scanning parameter and an image reconstructing parameter for respective scanning sequence after setting one or more scanning sequences for a region to be examined of a subject, where the scanning parameter includes at least one of the following: a voltage value and a current time product value of an X-ray tube, an X-ray beam collimation width, a ratio of a scanning bed moving speed with respect to an X-ray beam collimation width, a scanning gantry tilt angle, a scanning field of view, etc., and the image reconstructing parameter includes at least one of the following: an image thickness, an image interval, an image reconstructing field of view, a resolution, a filter parameter, and so on.

For performing a helical scanning process having a plurality of scanning sequences with a CT device, the scanning sequences will be executed one by one. In this case, if there is an overlap between scanning areas of different scanning sequences, the overlapping area will receive double scanning doses. On the one hand, there is a waste of scanning dose; on the other hand, when a subject is a human body, the excessive scanning dose may cause unwanted irradiation to the human body. To solve the above problems, the present disclosure proposes a method and device for multi-sequence scanning.

For ease of understanding, a method of multi-sequence scanning proposed in the present disclosure is first described below with reference to the scene diagram shown in FIG. 1.

Figure 1:
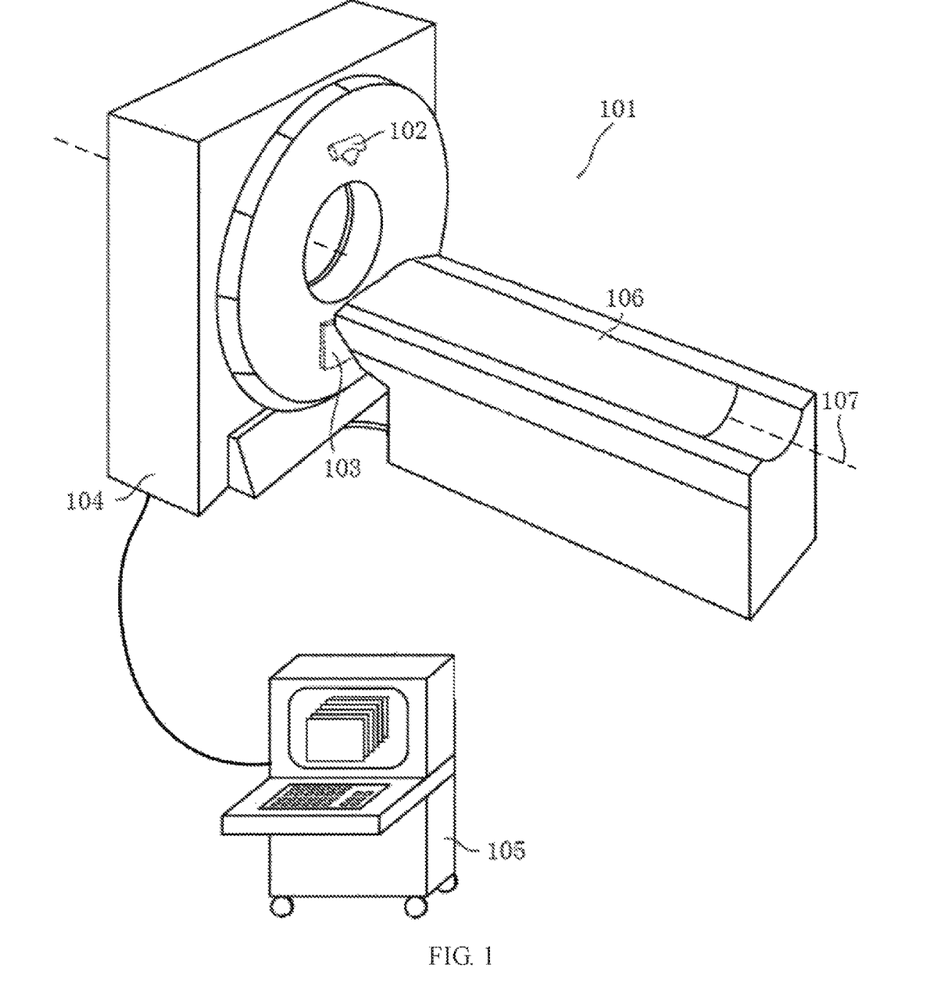
FIG. 1 illustrates a working scene of a CT device according to an example of the present disclosure.
Figure 2:
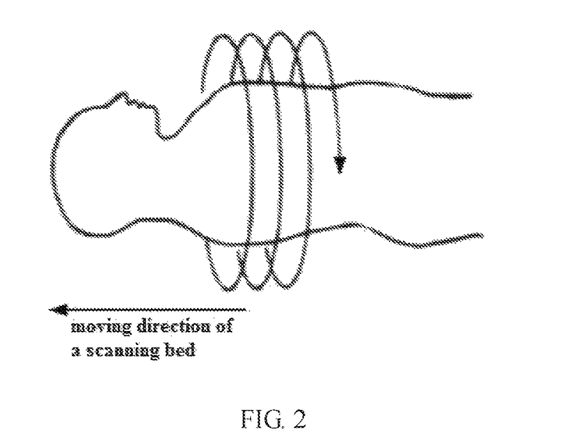
FIG. 2 illustrates a scanning trajectory of helical scanning according to an example of the present disclosure.

FIG. 1 is a working scene diagram of a CT device according to an example of the present disclosure, such as a CT device 101 as shown in FIG. 1 which is configured to perform the method of multi-sequence scanning proposed in the present disclosure. The CT device 101 may include an X-ray tube 102, a detector 103, a gantry 104, a computer 105, a scanning bed 106, and a system axis 107, where the X-ray tube 102 may be used to emit X-rays, the detector 103 may be used to detect the X-rays that have passed through a subject on the scanning bed 106, and the computer 105 may be used to provide a user with an interface for setting a scanning parameter and an image reconstruction parameter. Both the X-ray tube 102 and the detector 103 may be mounted on the gantry 104, the X-ray tube 102 is located opposite to the detector 103, and the X-ray tube 102 and the detector 103 may rotate at a constant speed with the system axis 107 as a central axis. A scanning hole may be provided in the gantry 104, and after the subject (such as a human body) is placed on the scanning bed 106, the scanning bed 106 may move along the system axis 107 and pass through the measuring field provided in the scanning hole in the scanning process so as to perform helical scanning with respect to the subject on the scanning bed 106, i.e., helical scanning. The scanning trajectory is helical as shown in FIG. 2.

Figure 3:
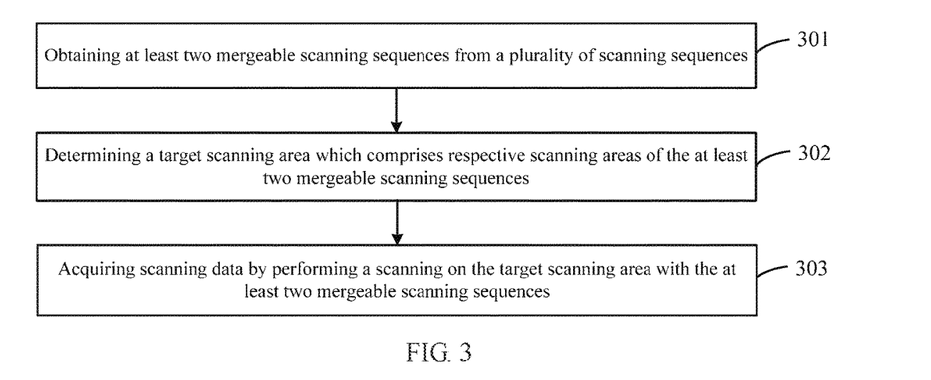
FIG. 3 illustrates a flow chart of a method of multi-sequence scanning according to an example of the present disclosure.

FIG. 3 is a flow chart of a method of multi-sequence scanning according to an example of the present disclosure. The method may include the following blocks.

At Block 301: at least two mergeable scanning sequences may be obtained from a plurality of scanning sequences.

Figure 4:
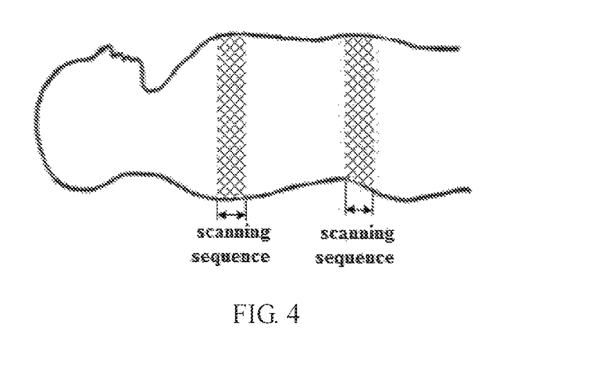
FIG. 4 illustrates a plurality of scanning sequences according to an example of the present disclosure.

One scanning sequence in the present example may correspond to one region to be examined of a subject. For example, the subject may be a human body. As shown in FIG. 4, two scanning sequences may correspond to two regions to be examined of the human body, respectively. In the diagnosis of the patient, a doctor may need to consider comprehensively CT images of the heart and the liver of the patient. At this time, the doctor may set two scanning sequences, one of which covers the heart of the patient and the other covers the liver of the patient, and then the doctor may control a CT device to perform helical scanning on the regions to be examined covered by the above two scanning sequences.

It is to be noted that, in the present example, a user may set a scanning sequence according to the position and size of a region to be examined of a subject. In addition, the present example does not limit the number of scanning sequences, i.e., theoretically, the user may set any number of scanning sequences.

The mergeable scanning sequences in the present example are sequences that may be scanned by a continuous helical scanning of a CT device once.

It is to be understood that, since the scanning dose is liable to be wasted when a helical scanning method is used to scan a plurality of scanning sequences, if a CT device can be controlled to scan a plurality of scanning sequences by performing a helical scanning once, this may play a positive role in improving the situation that the scanning dose is wasted.

In a feasible example, mergeable scanning sequences may be determined according to scanning parameters of scanning sequences and physical positional relationship between scanning areas corresponding to different scanning sequences.

For example, it may be assumed that a doctor sets the following scanning sequences for five regions to be examined of a patient: a scanning sequence A, a scanning sequence B, a scanning sequence C, a scanning sequence D and a scanning sequence E. Where, the scanning sequence A, the scanning sequence C and the scanning sequence D may have the same scanning parameter, and the scanning areas of every two adjacent scanning sequences in the three scanning sequences may overlap each other. At this time, the condition which indicates that two or more scanning sequences are mergeable may be defined as follows: the two or more scanning sequences have the same scanning parameter and there is an overlap between the scanning areas of every two adjacent scanning sequences in them. In this case, the scanning sequence A, the scanning sequence C and the scanning sequence D are determined as mergeable scanning sequences.

At block 302: a target scanning area may be determined, where the target scanning area includes respective scanning areas of the at least two mergeable scanning sequences.

In some examples of the disclosure, if the scanning sequence A, the scanning sequence C, and the scanning sequence D are all mergeable scanning sequences, the target scanning area includes scanning areas of the scanning sequence A, the scanning sequence C, and the scanning sequence D described above.

In some examples of the disclosure, a target scanning area covering all mergeable scanning sequences may be determined by the start positions and stop positions of the different mergeable scanning sequences.

At block 303: scanning data may be acquired by performing a scanning on the target scanning area.

As may be seen from the above example, at least two scanning sequences satisfying a preset mergeable condition may be identified from a plurality of scanning sequences and the at least two scanning sequences satisfying the preset mergeable condition may be scanned once, thereby preventing the overlapping area of the scanning areas from receiving double scanning doses. On the one hand, a waste of the scanning dose may be avoided; on the other hand, the irradiation to a human body may be minimized.

Figure 5:
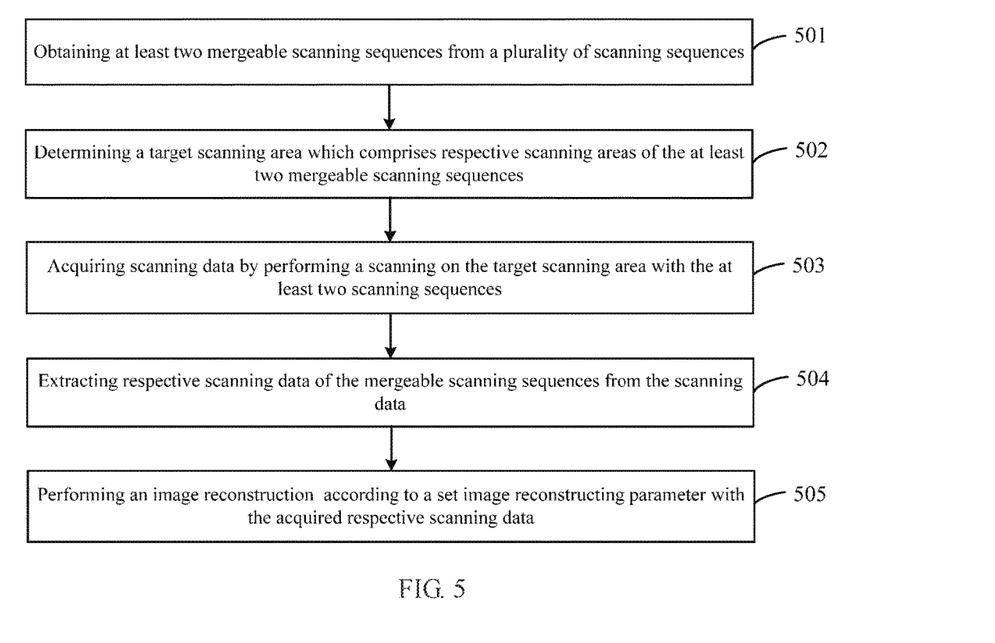
FIG. 5 illustrates a flow chart of a method of multi-sequence scanning according to another example of the present disclosure.

FIG. 5 is a flow chart of a method of multi-sequence scanning according to an example of the present disclosure. Taking into account the image reconstructing requirement of respective scanning sequence in the case of scanning a plurality of scanning sequences that have been merged, the method may include the following blocks.

At block 501: at least two mergeable scanning sequences may be obtained from a plurality of scanning sequences.

Since the scanning sequences and the mergeable scanning sequences in Block 501 of the example are substantially similar to the scanning sequences and the mergeable scanning sequences in Block 301 of the example shown in FIG. 3, the explanation of the above sequences is shown in the content of Block 301 in the example shown in FIG. 3, which will not be described again in the example.

In the present example, a preset mergeable condition for scanning sequences may be set according to the scanning parameter of scanning sequences and physical positional relationship between the scanning areas of different scanning sequences so as to identify the mergeable scanning sequences from a plurality of scanning sequences according to the preset mergeable condition. Specifically, the above Block 501 may include obtaining scanning sequences which satisfy a preset mergeable condition from the plurality of scanning sequences.

Where, the scanning sequences satisfying the preset mergeable condition may be mergeable scanning sequences. The preset mergeable condition may indicate that the at least two mergeable scanning sequences have a same scanning parameter and scanning areas of two adjacent scanning sequences in the at least two scanning sequences are overlapped. The scanning parameter in the present example may include at least one of the following: an X-ray tube voltage value kV, an X-ray tube current time product value mAs, an X-ray beam collimation width, a ratio of a scanning bed moving speed of a CT device with respect of an X-ray beam collimation width, a scanning gantry tilt angle, and a scanning field of view (Scan FOV).

The overlapping of the scanning areas of two adjacent scanning sequences in the present example may include at least one of the following: a start position of a first scanning sequence is located in a start-stop range of a second scanning sequence immediately before the first scanning sequence; and a stop position of the first scanning sequence is located in the start-stop range of the second scanning sequence.

It is to be noted that, in helical scanning, additional areas before and after respective scanning sequence may need to be scanned to obtain a desired image. A user may not intuitively observe the additional areas scanned (which are referred to as "pre-scanning areas" for convenience of description) and may only see the image inside the area of the scanning sequence (which is referred to as an "image area" in an example for convenience of description) through a positioning line.

In the present example, overlapping of scanning areas of the scanning sequences may be divided into two cases: overlapping of pre-scanning areas and overlapping of image areas.

Figure 6:
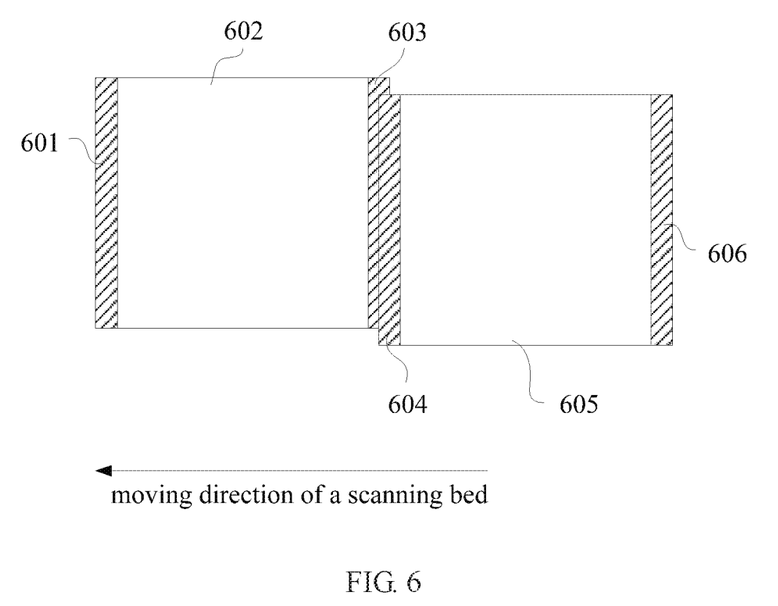
FIG. 6 illustrates overlapping of scanning areas according to an example of the present disclosure.

The case of overlapping of pre-scanning areas may be as shown in FIG. 6. In the figure, a scanning area of a first scanning sequence and a scanning area of a second scanning sequence are included, where the scanning areas of the first scanning sequence include a pre-scanning area 601, an image area 602, and a pre-scanning area 603, and the scanning areas of the second scanning sequence include a pre-scanning area 604, an image area 605, and a pre-scanning area 606. The pre-scanning area 603 and the pre-scanning area 604 are partially overlapped.

Figure 7:
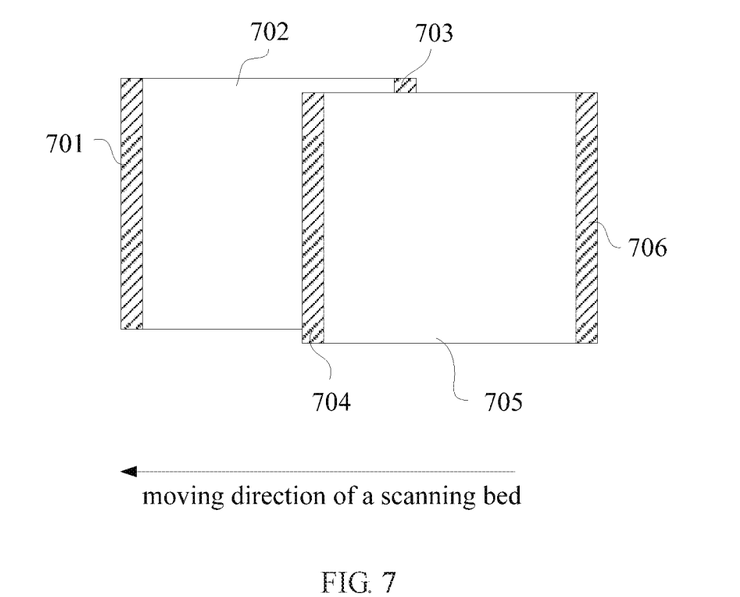
FIG. 7 illustrates overlapping of scanning areas according to another example of the present disclosure.

The case of overlapping of image areas is as shown in FIG. 7. In the figure, a scanning area of a first scanning sequence and a scanning area of a second scanning sequence are included, where the scanning areas of the first scanning sequence include a pre-scanning area 701, an image area 702, and a pre-scanning area 703, and the scanning areas of the second scanning sequence include a pre-scanning area 704, an image area 705, and a pre-scanning area 706. The image area 702 and the image area 705 are partially overlapped.

In some examples of the disclosure, it may be judged by the start position and/or stop position of a scanning sequence whether or not there is an overlap of the areas of adjacent scanning sequences. For convenience of description, "former scanning sequence" and "latter scanning sequence" are used to denote the adjacent scanning sequences. Such a judgement may specifically include:

judging whether or not the start position of a latter scanning sequence is located in a start-stop range of a former scanning sequence immediately before the latter sequence, if so, there is an overlap of the areas of the latter scanning sequence and the former scanning sequence; or judging whether or not the stop position of the latter scanning sequence is located in the start-stop range of the former scanning sequence, if so, there is an overlap of the areas of the latter scanning sequence and the former scanning sequence.

According to the direction of movement of a scanning bed in a CT device, scanning may be divided into forward scanning and backward scanning.

It is to be noted that, in an example, one end of a scanning bed near a scanning gantry is referred to as a bed head (a head support, an extension plate and other accessories may be inserted into the bed head), and the other end away from the scanning gantry is referred to as a bed tail.

In a forward scanning mode, the bed tail of the scanning bed is used as the origin of coordinates at this time and the direction in which the bed tail points to the bed head is a positive direction of the coordinates. If the former scanning sequence and the latter scanning sequence satisfy the following positional relationship, there is an overlap of the scanning areas of the former scanning sequence and the latter scanning sequence:

the stop position of the former scanning sequence≤the start position of the latter scanning sequence≤the start position of the former scanning sequence, or the stop position of the former scanning sequence≤the stop position of the latter scanning sequence≤the start position of the former scanning sequence.

In a backward scanning mode, the bed tail of the scanning bed is used as the origin of coordinates at this time and the direction in which the bed tail points to the bed head is a positive direction of the coordinates. If the former scanning sequence and the latter scanning sequence satisfy the following condition, there is an overlap of the scanning areas of the former scanning sequence and the latter scanning sequence:

the start position of the former scanning sequence≤the start position of the latter scanning sequence≤the stop position of the former scanning sequence, or the start position of the former scanning sequence≤the stop position of the latter scanning sequence≤the stop position of the former scanning sequence.

Both start and stop positions in the present example may be represented by bed code of a scanning bed corresponding to each scanning sequence. The bed code of the scanning bed may be understood as physical coding that is performed on the scanning bed by a user or a computer. For example, a one-dimensional coordinate system may be established with the bed tail of the scanning bed as the origin of coordinates and the direction in which the bed tail points to the bed head as a positive direction of the coordinates. At this time, a corresponding physical coordinate value i.e., physical coding, corresponds to each position of the scanning bed that is along the above positive direction of coordinates.

Figure 8:
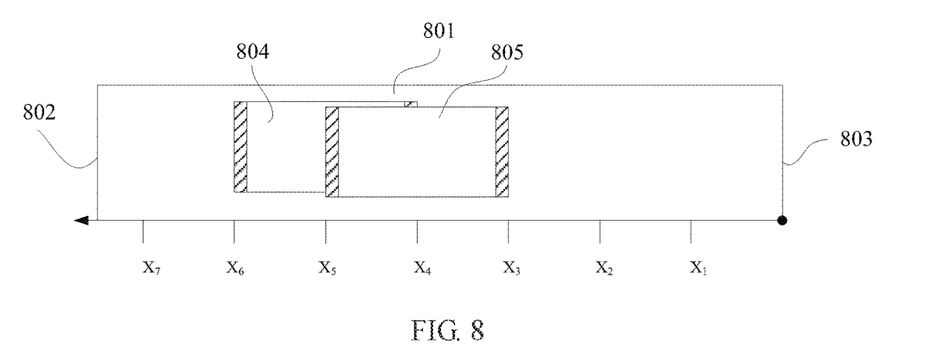
FIG. 8 illustrates physical coding for a scanning bed of a CT device according to an example of the present disclosure.

As shown in FIG. 8, a one-dimensional coordinate system may be established with the bed tail 803 of the scanning bed

801 of the CT device as the origin of the coordinates and the direction in which the bed tail 803 points to the bed head 802 as a positive direction of the coordinates. The scanning bed 801 has a corresponding physical coordinate value at each position along the positive direction of the coordinates (such as $X_1, X_2, X_3, X_4, X_5, X_6, X_7, \ldots$ as shown in FIG. 8). There are two scanning sequences on the scanning bed 801: a first scanning sequence 804 and a second scanning sequence 805. In a backward scanning mode, for the first scanning sequence 804, the start position is $X_4$ and the stop position is $X_6$, and for the second scanning sequence 805, the start position is $X_3$ and the stop position is $X_5$. It may be seen by comparing the start and/or stop positions of the first scanning sequence and the second scanning sequence that there is an overlap of the scanning areas of the first scanning sequence 804 and the second scanning sequence 805.

It is to be noted that, for convenience of understanding, in the present example, only two scanning sequences are taken as examples to introduce the method of judging whether there is an overlap of the scanning areas of the scanning sequences. In practical application, when the number of scanning sequences to be scanned is more than two, the judging method in the present example may be used where two adjacent scanning sequences are considered as a group to make judgement group by group. The present example is not limited thereto.

At block 502: a target scanning area may be determined, where the target scanning area includes respective scanning areas of the at least two mergeable scanning sequences.

In the present example, the start position and stop position of the target scanning area may be determined according to the start and stop positions of the above mergeable scanning sequences.

Both the start and stop positions in the present example may be represented by bed code of a scanning bed corresponding to each scanning sequence. Correspondingly, when the coded scanning bed is in a forward scanning mode:

the start position of the target scanning area may be equal to the start bed code of the mergeable scanning sequence closest to the bed head of the scanning bed, the stop position of the target scanning area may be equal to the stop bed code of the mergeable scanning sequence closest to the bed tail of the scanning bed; and in case of a backward scanning mode:

the start position of the target scanning area may be equal to the start bed code of the mergeable scanning sequence closest to the bed tail of the scanning bed, the stop position of the target scanning area may be equal to the stop bed code of the mergeable scanning sequence closest to the bed head of the scanning bed.

According to the above position determining rule, after a scanning range (i.e., the range between the start position of the scanning area and the stop position of the scanning area) of respective scanning sequence may be calculated, the maximum range of the superimposed scanning sequences is taken, so as to acquire the scanning start position and stop position of the target scanning area.

FIG. 8 is taken as an example again. There are the first scanning sequence 804 and the second scanning sequence 805 in the figure. For the first scanning sequence 804, the start position is $X_4$ and the stop position is $X_6$, and for the second scanning sequence 805, the start position is $X_3$ and the stop position is $X_5$. The scanning ranges of the first and second scanning sequences are superimposed to acquire the scanning start and stop positions ($X_3$, $X_6$) of the target scanning area covering the above two scanning sequences.

In some examples of the disclosure, the above block 502 may include determining a target scanning area directly when mergeable scanning sequences are included without confirmation from a user; the present example is not limited thereto.

At block 503: scanning data may be acquired by performing a scanning on the target scanning area with the at least two mergeable scanning sequences.

At block 504: respective scanning data of the mergeable scanning sequences may be extracted from the scanning data.

In the present example, the corresponding raw data (because the data are not image data, it is referred to as "raw data" for convenience of description) may be intercepted according to the start and stop positions of respective scanning sequence (specifically, according to the start and stop bed codes) from the scanning data acquired in block 503 and stored as raw data of corresponding scanning sequence.

It is to be noted that when a planned scanning direction (i.e., a scanning direction set by a user) does not coincide with an actual scanning direction, it is needed to mark the actual scanning direction in the raw data or to convert the data into the data of the planned direction. In practical application, any of the techniques known to those skilled in the art capable of achieving the above purpose of marking or converting may be used, which will not be described again in the present example.

At block 505: an image reconstruction may be performed according to the set image reconstructing parameter with the acquired scanning data.

In an example, the CT device may scan three sequences once: a first scanning sequence, a second scanning sequence, and a third scanning sequence; and the data acquired by the scanning may be raw data A; the raw data A1 corresponding to the first scanning sequence, the raw data A2 corresponding to the second scanning sequence, and the raw data A3 corresponding to the third scanning sequence are intercepted, respectively, and then image reconstruction may be performed on the raw data A1 according to the image reconstructing parameter C1 corresponding to the first scanning sequence to acquire a reconstructed image P1 corresponding to the first scanning sequence; image reconstruction may be performed on the raw data A2 according to the image reconstructing parameter C2 corresponding to the second scanning sequence to acquire a reconstructed image P2 corresponding to the second scanning sequence; and image reconstruction may be performed on the raw data A3 according to the image reconstructing parameter C3 corresponding to the third scanning sequence to acquire a reconstructed image P3 corresponding to the third scanning sequence.

As may be seen from the above example, for two or more scanning sequences with the same scanning parameter, if the scanning areas of the scanning sequences are overlapped or are relatively close in distance (overlapped in pre-scanning areas), in the example the entire covering range of these scanning sequences may be scanned continuously, and then the continuous raw data acquired by the scanning are split into raw data corresponding to respective scanning sequence and reconstructed, respectively, so as to avoid the overlapping part receiving double doses of irradiation.

In another example of the present disclosure, prior to determining a target scanning area, the following blocks may be added based on the example shown in FIG. 3 or FIG. 5:

outputting a message to request a user to agree with a merged scanning with respect of the at least two mergeable scanning sequences;

receiving an operation result from the user in response to the message, and triggering the execution of Block 302 or Block 502 to perform merged scanning on the target scanning area if the operation result indicates that the user agrees with the merged scanning.

In the present example, a message may be displayed on the display screen of a computer device in a CT device in the form of a graphical user interface, or played in the speaker of the computer device in the CT device in the form of voice, or output on the CT device in the form of lighting up an indicator light. The present example is not limited thereto.

When it is detected that the scanning parameter of a plurality of scanning sequences set by a user is the same and the scanning areas are overlapped, the user is prompted that "the CT device will finish scanning the mergeable scanning sequences continuously". After the user agrees, the CT device may finish scanning the area covered by the mergeable scanning sequences once.

It is to be noted that although the operation of the method of the present disclosure has been described in a particular order in the drawings, it is not intended or implied that these operations must be performed in that particular order or that all of the operations shown must be performed to achieve the desired result. In contrast, the executing order of the blocks depicted in the flow chart may be changed. Additionally or alternatively, some blocks may be omitted, a plurality of blocks may be combined into one block, and/or one block may be divided into a plurality of sub-blocks for execution.

Corresponding to the examples of the method of multi-sequence scanning proposed in the present disclosure, the present disclosure also proposes an example of a device for multi-sequence scanning.

Figure 9:
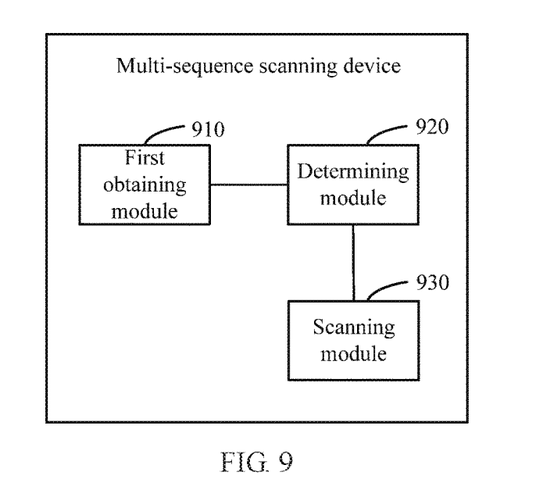
FIG. 9 illustrates a block diagram of control logic for multi-sequence scanning according to an example of the present disclosure.

FIG. 9 is a block diagram of control logic for multi-sequence scanning according to an example of the present disclosure. The device may include:

a first obtaining module 910 configured to obtain at least two mergeable scanning sequences from a plurality of scanning sequences;

a determining module 920 configured to determine a target scanning area, where the target scanning area includes scanning areas of the at least two mergeable scanning sequences obtained by the first obtaining module 910; and a scanning module 930 configured to acquire scanning data by performing a scanning on the target scanning area determined by the determining module 920.

As may be seen from the above example, at least two scanning sequences satisfying a preset mergeable condition may be identified from a plurality of scanning sequences and the at least two scanning sequences satisfying the preset mergeable condition may be scanned at once, thereby preventing the overlapping area of the scanning areas from receiving double scanning doses. On the one hand, a waste of the scanning dose may be avoided; on the other hand, the irradiation to a human body may be minimized.

Figure 10:
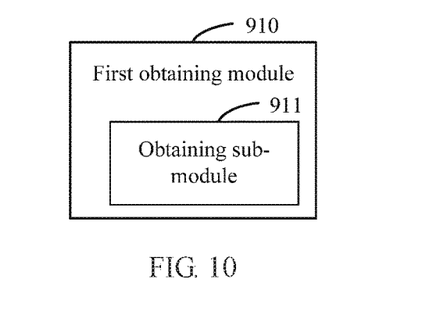
FIG. 10 illustrates a block diagram of the first obtaining module which is shown in FIG. 9.

FIG. 10 is a block diagram of the first obtaining module 910 which is shown in FIG. 9. As shown in FIG. 10, the first obtaining module 910 may include an obtaining sub-module 911 which is configured to obtain scanning sequences satisfying a preset mergeable condition from a plurality of scanning sequences. Where, the scanning sequences satisfying a preset mergeable condition are mergeable scanning sequences. The preset mergeable condition indicates that the at least two mergeable scanning sequences have a same scanning parameter and scanning areas of two adjacent scanning sequences in the at least two scanning sequences are overlapped.

In the example, the scanning parameter may include at least one of an X-ray tube voltage value, an X-ray tube current time product value, an X-ray beam collimation width, a ratio of a scanning bed moving speed of a CT device with respect to an X-ray beam collimation width, a scanning gantry tilt angle, and a scanning field of view.

In another example of the present disclosure, the overlapping of the scanning areas of two adjacent scanning sequences may include at least one of: a start position of a first scanning sequence is located in a start-stop range of a second scanning sequence immediately before the first scanning sequence; and a stop position of the first scanning sequence is located in the start-stop range of the second scanning sequence.

Figure 11:
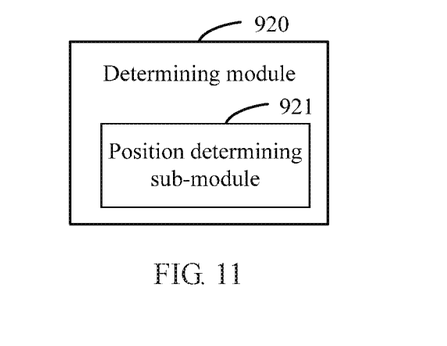
FIG. 11 illustrates a block diagram of the determining module which is shown in FIG. 9.

FIG. 11 is a block diagram of the determining module 920 which is shown in FIG. 9. In the example, the determining module 920 may include a position determining sub-module 921 configured to determine the start position and stop position of the target scanning area according to the start positions and stop positions of the mergeable scanning sequences.

Figure 12:
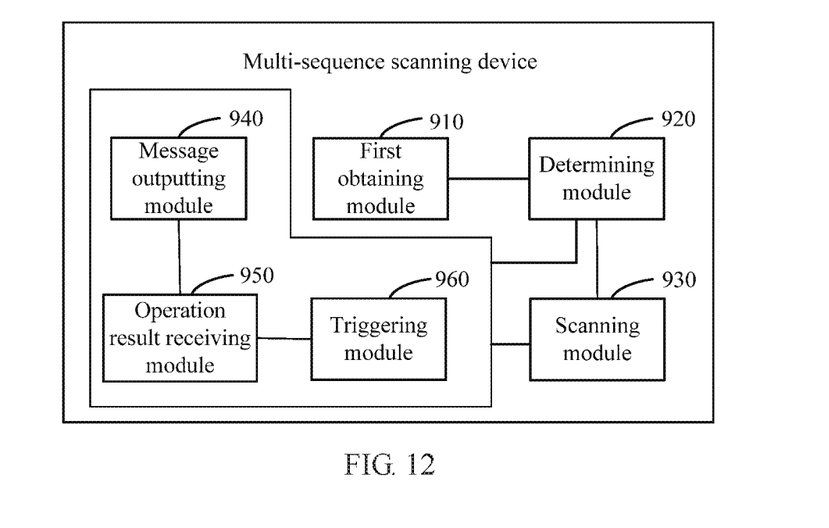
FIG. 12 illustrates a block diagram of control logic for multi-sequence scanning according to another example of the present disclosure.

FIG. 12 is a block diagram of control logic for multi-sequence scanning according to another example of the present disclosure. The example is on the basis of the example shown in FIG. 9, and in the example the device may further include:

a message outputting module 940 configured to output a message to request a user to agree with a merged scanning of the at least two mergeable scanning sequences;

an operation result receiving module 950 configured to receive an operation result from the user in response to the message output by the message outputting module 940; and a triggering module 960 configured to trigger the scanning module 930 to scan the target scanning area if the operation result received by the operation result receiving module 950 indicates that the user agrees to perform the merged scanning.

Figure 13:
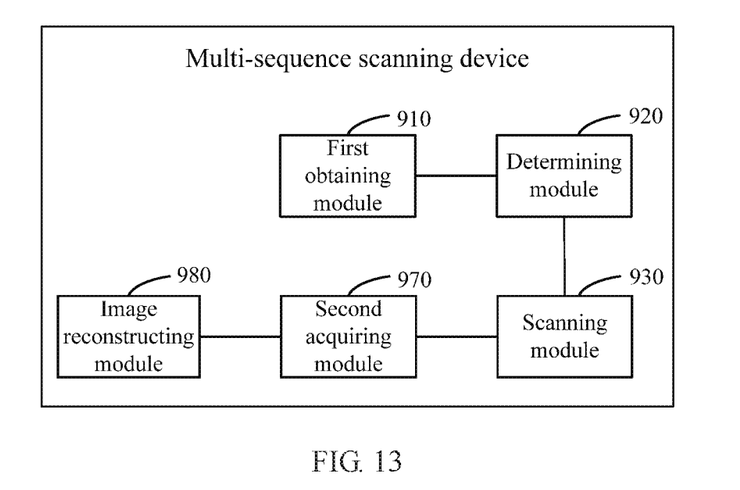
FIG. 13 illustrates a block diagram of control logic for multi-sequence scanning according to a still another example of the present disclosure.

FIG. 13 is a block diagram of control logic for multi-sequence scanning according to a still another example of the present disclosure. On the basis of the example shown in FIG. 9, the device may further include:

a second acquiring module 970 configured to acquire respective scanning data of the mergeable scanning sequences from the scanning data from the scanning module 930; and an image reconstructing module 980 configured to perform an image reconstruction according to the set image reconstructing parameter on different scanning data acquired by the second acquiring module 970.

The implementation of the functions and effects of each of the modules in the above device are described in detail in the implementation of the corresponding blocks in the above method, which will not be described again herein.

For the device example, since it corresponds substantially to the method embodiment, reference is made to the partial description of the method embodiment for the related part. The device embodiment described above is merely illustrative, where the unit described as separate components may or may not be physically separate, and the component shown as a unit may or may not be a physical unit, which may be located in one place or may be distributed to multiple network units. A part or all of the modules may be selected according to the actual needs to achieve the object of the solution of the present disclosure. One of ordinary skill in the art will understand and practice without making creative work.

Figure 14:
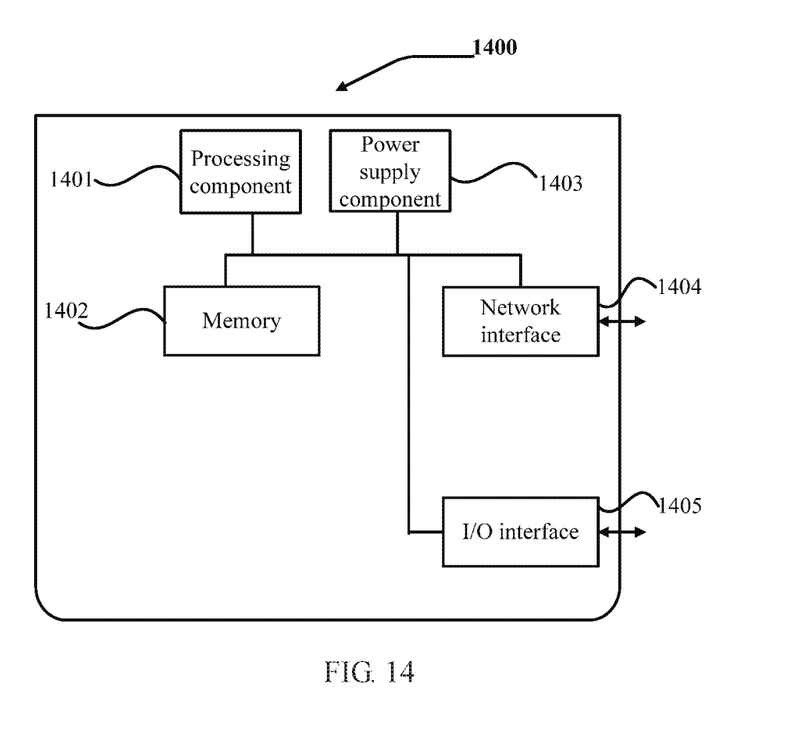
FIG. 14 illustrates a structure of a medical device 1400 according to an example of the present disclosure.

The present disclosure further provides a device for multi-sequence scanning which may be applied to a medical device including a CT device and a PET device and so on. FIG. 14 is a structure schematic diagram of a medical device 1400 according to an example of the disclosure. Referring to FIG. 14, the medical device 1400 may include a processing component 1401 that further includes one or more processors and a memory resource represented by a memory 1402 for storing instructions that may be executed by the processing component 1401, such as an application program. The application program stored in the memory 1402 may include one or more modules, each of which is corresponding to a set of instructions.

In an example of the present disclosure, the device for multi-sequence scanning may be located in the memory 1402 and the processing component 1401 may perform the method of multi-sequence scanning of the present example by the device for multi-sequence scanning so as to perform continuous scanning on a subject.

The medical device 1400 may further include a power supply component 1403 configured to perform power management for the medical device 1400, a wired or wireless network interface 1404 configured to connect the medical device 1400 to a network, and an Input/Output (I/O) interface 1405.

The foregoing is intended only as examples of the present disclosure and is not intended to be limiting of the present disclosure, and any modifications, equivalent substitutions, improvements, and so on, which are made within the spirit and principles of the present disclosure, should fall within the scope of protection of the present disclosure.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

The figures are only illustrations of an example, wherein the units or procedure shown in the figures are not necessarily essential for implementing the present disclosure. Those skilled in the art will understand that the units in the device in the example may be arranged in the device in the examples as described, or may be alternatively located in one or more devices different from that in the examples. The units in the examples described may be combined into one module or further divided into multiple sub-units.

Although the flow charts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the following description, numerous specific details are set forth to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Throughout the present disclosure, the word "include", or variations such as "includes" or "including", will be understood to imply the inclusion of a stated element, integer or block, or group of elements, integers or blocks, but not the exclusion of any other element, integer or block, or group of elements, integers or blocks.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of multi-sequence scanning, comprising:
    obtaining at least two scanning sequences satisfying a preset mergeable condition from a plurality of scanning sequences, wherein the preset mergeable condition indicates that the at least two scanning sequences have a same scanning parameter and scanning areas of two adjacent scanning sequences in the at least two scanning sequences are overlapped;
    taking the obtained scanning sequences satisfying the preset mergeable condition as at least two mergeable scanning sequences;
    determining a target scanning area which comprises respective scanning areas of the at least two mergeable scanning sequences; and
    acquiring scanning data by performing a scanning on the target scanning area with the at least two mergeable scanning sequences.

2. The method according to claim 1, wherein the scanning parameter comprises at least one of:
    an X-ray tube voltage value,
    an X-ray tube current time product value,
    an X-ray beam collimation width,
    a ratio of scanning bed moving speed with respect to an X-ray beam collimation width,
    a scanning gantry tilt angle, and
    a scanning field of view.

3. The method according to claim 1, wherein the overlapping for the scanning areas of two adjacent scanning sequences comprises at least one of:
    a start position of a first scanning sequence being located in a start-stop range of a second scanning sequence immediately before the first scanning sequence; and
    a stop position of the first scanning sequence being located in the start-stop range of the second scanning sequence.

4. The method according to claim 1, wherein determining the target scanning area comprises:
    determining a start position and a stop position of the target scanning area according to respective start positions and stop positions of the at least two mergeable scanning sequences.

5. The method according to claim 1, further comprising:
    outputting a message to request a user to agree with a merged scanning with respect to the at least two mergeable scanning sequences;
    receiving an operation result from the user in response to the message; and performing the merged scanning on the target scanning area if the operation result indicates that the user agrees with the merged scanning.

6. The method according to claim 1, further comprising:
extracting respective scanning data of the mergeable scanning sequences from the scanning data; and
performing an image reconstruction according to a set image reconstructing parameter with the extracted respective scanning data.

7. A device for multi-sequence scanning, comprising:
a processor, and
a machine-readable storage medium to store machine-executable instructions corresponding to control logic for multi-sequence scanning,
wherein, by reading and executing the machine-executable instructions, the processor is caused to:
obtain at least two scanning sequences satisfying a preset mergeable condition from a plurality of scanning sequences, wherein the preset mergeable condition indicates that the at least two scanning sequences have a same scanning parameter and scanning areas of two adjacent scanning sequences in the at least two scanning sequences are overlapped;
take the obtained scanning sequences satisfying the preset mergeable condition as at least two mergeable scanning sequences;
determine a target scanning area which comprises respective scanning areas of the at least two mergeable scanning sequences; and
acquire scanning data by performing a scanning on the target scanning area with the at least two mergeable scanning sequences.

8. The device according to claim 7, wherein the scanning parameter comprises at least one of:
an X-ray tube voltage value,
an X-ray tube current time product value,
an X-ray beam collimation width,
a ratio of scanning bed moving speed with respect to an X-ray beam collimation width,
a scanning gantry tilt angle, and
a scanning field of view.

9. The device according to claim 7, wherein the overlapping for the scanning areas of two adjacent scanning sequences comprises at least one of:
a start position of a first scanning sequence is located in a start-stop range of a second scanning sequence immediately before the first scanning sequence; and
a stop position of the first scanning sequence is located in the start-stop range of the second scanning sequence.

10. The device according to claim 7, wherein when determining the target scanning area, the machine-executable instructions cause the processor to:
determine a start position and a stop position of the target scanning area according to respective start positions and stop positions of the at least two mergeable scanning sequences.

11. The device according to claim 7, wherein the machine-executable instructions further cause the processor to:
output a message to request a user to agree with a merged scanning with respect to the at least two mergeable scanning sequences;
receive an operation result from the user in response to the message; and
perform the merged scanning on the target scanning area if the operation result indicates that the user agrees with the merged scanning.

12. The device according to claim 7, wherein the machine-executable instructions further cause the processor to:
extract respective scanning data of the mergeable scanning sequences from the scanning data; and
perform an image reconstruction according to a set image reconstructing parameter with the extracted respective scanning data.

13. A non-volatile machine-readable storage medium having machine-executable instructions executable by one or more processors stored thereon, wherein the machine-executable instructions cause the processor to:
obtain at least two scanning sequences satisfying a preset mergeable condition from a plurality of scanning sequences, wherein the preset mergeable condition indicates that the at least two scanning sequences have a same scanning parameter and scanning areas of two adjacent scanning sequences in the at least two scanning sequences are overlapped;
take the obtained scanning sequences satisfying the preset mergeable condition as at least two mergeable scanning sequences;
determine a target scanning area which comprises respective scanning areas of the at least two mergeable scanning sequences; and
acquire scanning data by performing a scanning on the target scanning area with the at least two mergeable scanning sequences.

* * * * *